United States Patent [19]

Kane

[11] 4,384,126
[45] May 17, 1983

[54] SYNTHESIS OF DEOXYZOAPATANOL DERIVATIVES

[75] Inventor: Vinayak V. Kane, Tucson, Ariz.

[73] Assignee: Ortho Pharmaceutical Corporation, Raritan, N.J.

[21] Appl. No.: 348,469

[22] Filed: Feb. 12, 1982

[51] Int. Cl.³ .......................................... C07D 313/04
[52] U.S. Cl. .................................. 549/346; 549/341; 549/271; 549/222; 549/334; 568/329
[58] Field of Search ........................................ 549/346

[56] References Cited

U.S. PATENT DOCUMENTS 4,237,053 12/1980 Kane .................................... 549/346
4,239,689 12/1980 Kane .................................... 549/346

Primary Examiner—Norma S. Milestone
Attorney, Agent, or Firm—Benjamin F. Lambert

[57] ABSTRACT

A method for the synthesis of derivatives of deoxyzoapatanol is described. The derivatives are effective as post-implantive contragestational agents.

8 Claims, No Drawings

SYNTHESIS OF DEOXYZOAPATANOL DERIVATIVES

The present invention relates to a method of synthesizing deoxyzoapatanol derivatives.

In U.S. Pat. No. 4,086,358 a method is described for the isolation of the active ingredients in the zoapatle plant. One of the active ingredients is 2S,3R-6E(2-hydroxyethylidene)-2-methyl-2-(4',8'-dimethyl-5'-oxo-7-nonenyl)oxepan-3-ol and is commonly referred to as zoapatanol. The deoxyzoapatanol derivative, which is the subject of this invention, 6-(2'-hydroxyethylidene)-2-methyl-2-(4',8'-dimethyl-5'-hydroxy-7'-nonenyl)oxepane, has the following structure:

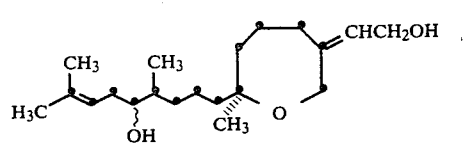

The compound is a mixture of the 6-E and 6-Z isomers. For the sake of simplicity, only one isomer has been depicted.

The deoxyzoapatanol derivative is prepared according to the scheme outlined below.

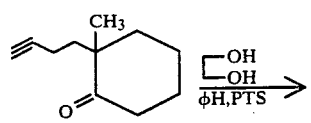

1

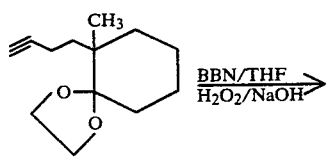

2

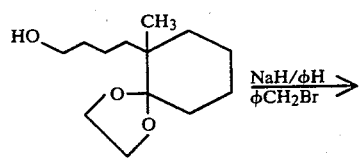

3

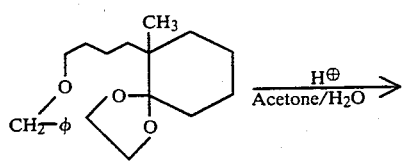

4

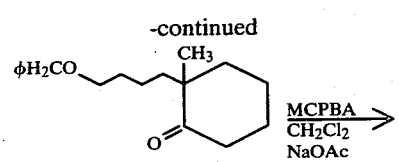

5

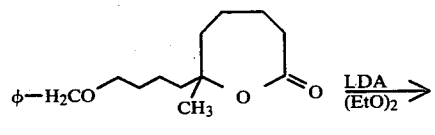

6

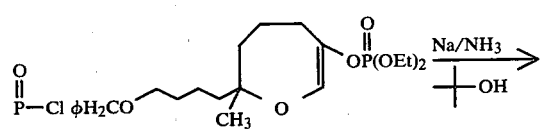

7

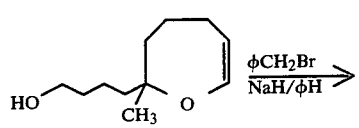

8

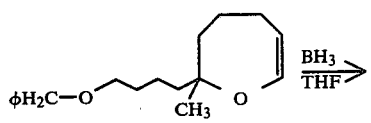

9

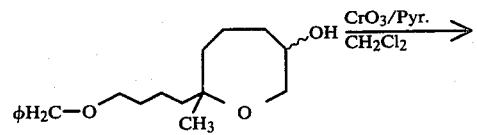

10

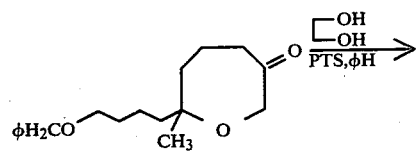

11

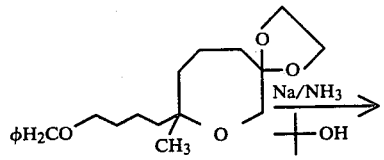

12

4,384,126
3
-continued
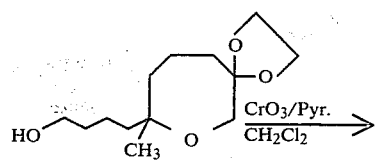
13
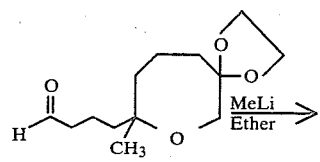
14
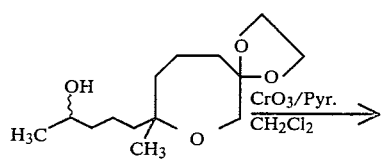
15
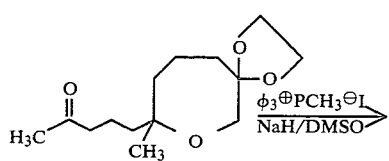
16
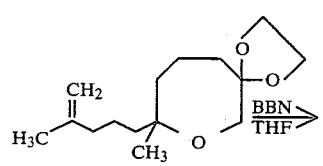
17
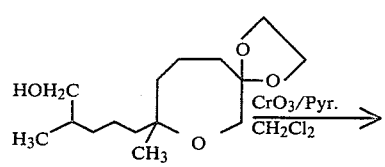
18
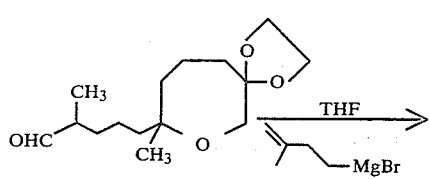
19
4
-continued
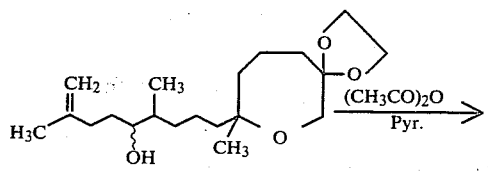
20
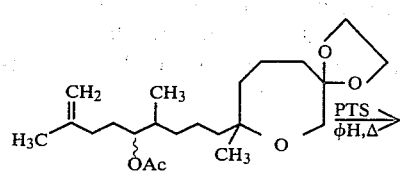
21
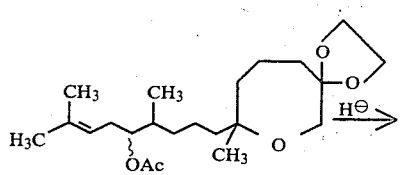
22
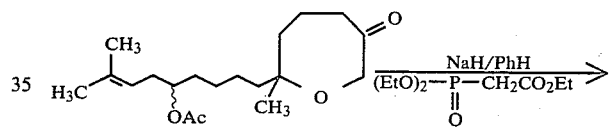
23
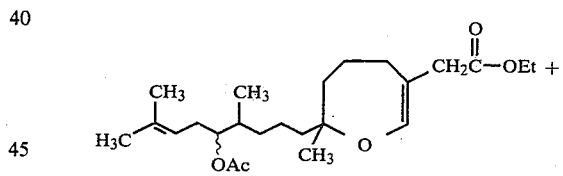
24
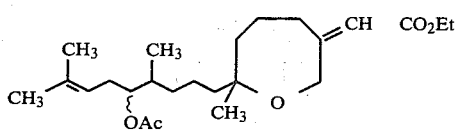
25
24 + 25 $\xrightarrow{\text{LiAlH}_4}{\text{Ether}}$
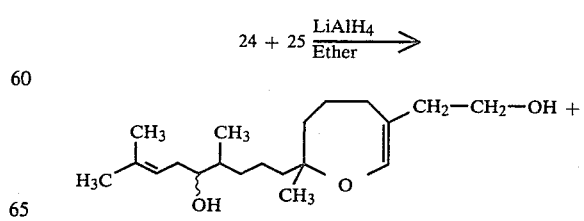
26

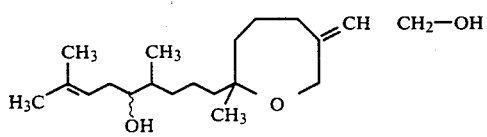

27

The first step in the preparation of the deoxyzoapatanol derivative (27) involves the reaction of a 2-(3'-butynyl)-cyclohexanone (1) with ethylene glycol to form a ketal (2). The reaction is carried out in a suitable solvent such as benzene, toluene or xylene. It is preferred to carry out the reaction at the reflux temperature of the solvent and in the presence of an acid such as, for example, p-toluenesulfonic acid, camphorsulfonic acid, napthalenesulfonic acid and oxalic acid. The ketal (2) is then converted to the (4'-hydroxybutyl)-cyclohexane derivative (3) by first reacting it with 9-borabicyclo[3.3.1]nonane in a suitable solvent such as tetrahydrofuran, ether, diethyl ether and diisopropyl ether. The reaction mixture is then reacted with hydrogen peroxide in the presence of a base such as sodium hydroxide or potassium hydroxide. A 30% aqueous hydrogen peroxide solution is preferred for this step in the reaction sequence. The alcohol (3) is then converted to the benzyl ether (4) by reaction with benzyl bromide in the presence of a base such as sodium hydride, potassium hydride and lithium diisopropylamide in tetrahydrofuran. Treatment of the (4'-benzyloxybutyl)-1,1-ethylenedioxycyclohexane compound (4) with strong acid yields the corresponding ketone (5). Strong acids such as sulfuric acid, p-toluenesulfonic acid, or camphorsulfonic acid in a wet solvent such as tetrahydrofuran, benzene or acetone may be employed. The reaction temperature is about 50° C.

The 2-methylcyclohexanone derivative (5) is then converted to the 7-methyl-1-oxa-cycloheptan-2-one derivative (6) by reaction with m-chloroperoxybenzoic acid. The reaction is preferably carried out in the presence of a mild base such as sodium acetate or sodium bicarbonate. Solvents which can be employed for the reaction include methylene chloride, dichloroethane and chloroform.

The oxepinyl phosphate derivative (7) is prepared from the lactone (6) by reaction with diethyl chlorophosphate in the presence of lithium diisopropylamide in a suitable solvent such as tetrahydrofuran or a mixture of tetrahydrofuran-ether in a ratio of about 80:20. Reaction of the oxepinyl phosphate (7) with sodium in liquid ammonia gives the methyl hydroxybutyl oxepane (8). Reaction of the methyl hydroxybutyl oxepane (8) with benzyl bromide in the presence of a base such as sodium hydride, potassium hydride and lithium diisopropylamide in tetrahydrofuran, for example, gives the corresponding benzyloxy-2-methyl-6-oxepene (9). The reaction is carried out in a suitable solvent such as, for example, benzene, dimethoxyethane, tetrahydrofuran or 80/20 mixtures of these solvents, and preferably at 50° C. in an inert atmosphere such as nitrogen. Reaction of the benzyloxybutyl oxepene (9) with diborane ($B_2H_6$) yields the corresponding alcohol (10). The reaction can be carried out at room temperature. Suitable solvents for the reaction include tetrahydrofuran, ether and dimethoxyethane and mixtures of ether and tetrahydrofuran. Oxidation of the alcohol (10) yields the corresponding ketone (11). Oxidizing agents which can be employed include pyridine-chromium trioxide in a solvent such as methylene chloride, chromic acid-sulfuric acid in aqueous acetone (Jones Reagent). Reaction of the ketone (11) with ethylene glycol yields the corresponding benzyloxybutyl ethylenedioxy derivative (12). The reaction is preferably carried out at the reflux temperature of the solvent. Solvents such as benzene, toluene and xylene can be employed. The benzyloxybutyl ethylenedioxy derivative (12) is converted to the ethylenedioxy hydroxybutyl derivative (13) by reaction with sodium in liquid ammonia. Removal of the benzyl protecting group can also be carried out with palladium on charcoal (15%) or palladium on calcium carbonate (10%) in solvents such as ethyl alcohol and ethyl acetate. Oxidation of the hydroxybutyl derivative (13) with a suitable oxidizing agent such as, for example, pyridine-chromium trioxide, yields the ethylenedioxy oxobutyl oxepane (14). The oxidation is carried out in a suitable solvent such as methylene chloride. Reaction of the oxobutyl oxepane derivative with methyllithium yields the corresponding hydroxypentyl methyl oxepane derivative (15). Solvents which can be employed for the reaction include hexane, ether and pentane. The reaction is preferably carried out at a temperature between 0° C. and room temperature in an inert atmosphere such as nitrogen. Oxidation of the hydroxypentyl methyl oxepane (15) yields the corresponding oxopentyl methyl oxepane (16). Suitable oxidizing agents include pyridine-chromium trioxide, and Jones Reagent. The preferred solvent for the oxidation reaction is methylene chloride. The reaction is preferably carried out at a temperature between 5° C. and room temperature. The oxopentyl methyl oxepane (16) is then reacted with triphenylmethylphosphonium iodide to form a methyl pentenyl oxepane (17). The reaction is carried out in the presence of a base such as, for example, sodium hydride in a suitable solvent such as dimethylsulfoxide. The conversion of 16 to 17 can also be carried out using butyl lithium in ether. Reaction of the pentenyl oxepane (17) with 9-borabicyclo[3.3.1]nonane yields the corresponding hydroxypentyl oxepane (18). The reaction is carried out at a temperature between 0° C. and room temperature. Solvents which can be employed include methylene chloride, tetrahydrofuran, ether and diisopropyl ether or mixtures of solvents such as tetrahydrofuran and ether. The conversion of 16 to 17 can also be carried out with triphenylmethylphosphonium iodide using butyllithium in ether. Sodium hydride and potassium hydride in benzene may also be employed.

Oxidation of the hydroxypentyl oxepane (18) with a suitable oxidizing agent such as, for example, pyridine-chromium trioxide in methylene chloride yields the oxopentyl oxepane derivative (19). Reaction of the oxopentyl oxepane derivative with a Grignard reagent prepared from 4-bromo-3-methyl-1-butene yields the hydroxy nonenyl compound (20). Suitable solvents for the Grignard reaction include tetrahydrofuran, diethyl ether and dimethoxyethane. Reaction of the hydroxy nonenyl compound (20) with an esterifying agent yields the corresponding ethylenedioxy-dimethyl-8'-nonenyl ester (21). Esterifying agents which can be employed include lower alkyl anhydrides such as acetic anhydride, propionic anhydride, butyric anhydride and the like. The esterification reaction is preferably carried out in pyridine. Reaction of the ethylenedioxy 8'-nonenyl ester (21) with an acid such as p-toluenesulfonic acid, for example, in a suitable solvent such as benzene yields the isomeric 7'-nonenyl ester (22). Upon treatment of the 7'-nonenyl ester (22) with an acid such as p-toluenesulfonic acid in a suitable solvent mixture such as aqueous acetone or aqueous tetrahydrofuran, the corresponding ketone (23) is obtained. The reaction is preferably carried out at the reflux temperature of the solvent. The ketone (23) is then reacted with triethylphosphonoacetate in the presence of sodium hydride, potassium hydride, or lithium diisopropylamide in tetrahydrofuran to form a mixture of esters (24 and 25). The reaction is carried out in a suitable solvent such as benzene, dimethoxyethane or tetrahydrofuran and preferably at a temperature between room temperature about 80° C., depending upon the solvent employed, in an inert atmosphere such as nitrogen.

Reduction of the esters with a suitable reducing agent such as lithium aluminum hydride, for example, yields the corresponding alcohols (26 and 27). Solvents which can be employed for the reduction include ether, diisopropyl ether and tetrahydrofuran and the like. The reaction is preferably carried out in an inert atmosphere such as nitrogen. Column chromatography over SilicAR CC-7 serves as a means of separating the mixture and purifying the compounds obtained from the mixture.

The novel compounds (26 and 27) are effective as post-implantive contragestational agents.

EXAMPLE 1

2-(3'-Butynyl)-1,1-ethylenedioxy-2-methylcyclohexane (2)

A mixture of 2-(3'-butynyl)-2-methylcyclohexanone (26.55 g. 0.162 mol), ethylene glycol (50 ml) and p-toluenesulfonic acid (600 mg) in benzene (600 ml) is refluxed for 20 hours using a Dean-Stark apparatus. The cooled solution is diluted with water (500 ml) and diethyl ether (500 ml). The organic layer is separated and the aqueous layer is extracted with ether (2×500 ml). The combined organic layers are washed with satd. NaHCO₃ (2×500 ml), satd. NaCl, and dried (MgSO₄). The solvents are removed at reduced pressure and the crude product (33.9 g) is chromatographed on SilicAR CC-7 (410 g, Mallinckrodt) in hexane. Elution with 5% ethyl acetate/hexane gives 2-(3'-butynyl)-1,1-ethylenedioxy-2-methylcyclohexane (2) as a colorless oil (30.5 g, 91%): ir(neat), 2133 cm⁻¹ (C≡C), nmr (CDCl₃)δ0.95 (s, 3H, CH₃), 3.98 (s, 4H, ketal).

EXAMPLE 2

1,1-Ethylenedioxy-2-(4'-hydroxybutyl)-2-methylcyclohexane (3)

A solution of 2-(3'-butynyl)-1,1-ethylenedioxy-2-methylcyclohexane (30.5 g, 0.147 mol) in dry tetrahydrofuran (200 ml) is added to a stirred solution of 9-borabicyclo[3.3.1]nonane (37.6 g 0.307 mol) in dry tetrahydrofuran (800 ml) maintained at 0° in a nitrogen atmosphere. After the addition is complete the mixture is stirred for 1 hour at 25° C. The reaction mixture is then cooled to 0° C., 3 N NaOH (147 ml, 0.44 mol) followed by 30% H₂O₂ (166.2 g, 1.46 mol) are added while maintaining the temperature at 0° C. After the addition is complete the mixture is stirred for 1 hour at 25° C., diluted with satd. NaCl (2000 ml), extracted with ether (5×800 ml) and dried (MgSO₄). The solvents are removed under reduced pressure and the crude product (70 g) is chromatographed on SilicAR CC-7 (590 g) in hexane. Elution with 10–15% ethyl acetate/hexane gives 1,1-ethylenedioxy-2-(4'-hydroxybutyl)-2-methylcyclohexane as a colorless oil (31 g, 93%): ir(neat) 3433 cm⁻¹ (OH), nmr (CDCl₃)δ0.93 (s, 3H, CH₃), 2.00 (s, 1H, OH), 3.62 (t, 2H, HO—CH₂—CH₂), 3.96 (s, 4H, ketal).

EXAMPLE 3

2-(4'-Benzyloxybutyl)-1,1-ethylenedioxy-2-methylcyclohexane (4)

A solution of 1,1-ethylenedioxy-2-(4'-hydroxybutyl)-2-methylcyclohexane (26 g, 0.136 mol.) in benzene (100 ml) is added to a suspension of sodium hydride (6.53 g, 0.272 mol; 13.05 g of a 50% mineral oil dispersion freshly washed with pentane and benzene) in benzene (500 ml) in a nitrogen atmosphere. After 30 minutes benzylbromide (35 g, 020 mol) in benzene (100 ml) is added and the reaction is heated at reflux for 20 hours. The reaction mixture is cooled to room temperature and diluted with water (100 ml) and ether (500 ml). The organic layers are separated and washed with satd. NaCl (2×400 ml) and dried (MgSO₄). The solvents are removed under reduced pressure and the crude product is chromatographed on SilicAR CC-7 (575 g) in hexane. Elution with 5% ethyl acetate/hexane gives 2-(4'-benzyloxybutyl)-1,1-ethylenedioxy-2-methylcyclohexane as a slightly yellowish oil (32.45 g, 90%): nmr (CDCl₃)δ0.98 (s, 3H, CH₃), 3.5 (t, 2H, —O—CH₂—CH₂), 3.98 (s, 4H, ketal) 4.44 (s, 2H, O—CH₂—Ph), 7.3 (s, 5H, aromatic).

EXAMPLE 4

2-(4'-Benzyloxybutyl)-2-methylcyclohexanone (5)

A mixture of the 2-(4'-benzyloxybutyl)-1,1-ethylenedioxy-2-methylcyclohexane (32.5 g, 0.10 mol), acetone (375 ml), H₂O (50 ml) and 0.002 N H₂SO₄ (125 ml) is refluxed for 18 hours under a nitrogen atmosphere. The reaction mixture is cooled, the acetone is evaporated under reduced pressue and the aqueous layer extracted with ether (3×500 ml). The combined organic layers are washed with satd. NaHCO₃ (2×300 ml), satd. NaCl (2×500 ml) and dried (MgSO₄). The solvents are removed under reduced pressure and the crude product (29 g) is chromatographed on SilicAR CC-7 (500 g) in hexane. Elution with 5% ethyl acetate/hexane gives 2-(4'-benzyloxybutyl)-2-methylcyclohexanone as a colorless oil (25.4 g, 91%): ir (neat) 1705 cm⁻¹ (CO); nmr (CDCl₃) δ1.03 (s, 3H, CH₃), 2.35 (m, 2H, OC—CH₂—CH₂), 3.5 (t, 2H, O—CH₂—CH₂), 4.44 (s, 2H, O—CH₂—Ph), 7.3 (s, 5H, aromatic).

EXAMPLE 5

7-(4'-Benzyloxybutyl)-7-methyl-1-oxa-cycloheptan-2-one (6)

A solution of 2-(4'-benzyloxybutyl)-2-methylcyclohexanone (25.2 g, 0.092 mol), sodium acetate (8.2 g, 0.1 mol), m-chloroperoxybenzoic acid 85% (24.2 g, 0.12 mol) and distilled methylene chloride (1200 ml) is heated at reflux under a nitrogen atmosphere for 7 hours. The solution is cooled and filtered and the filtrate is washed with satd. NaHCO₃, satd. NaCl, and dried (MgSO₄). The solvent is removed under reduced pressure and the crude product (30.6 g) is chromatographed on SilicAR CC-7 (600 g) in hexane. Elution with 20% ethyl acetate/hexane gives 7-(4'-benzyloxybutyl)-7-methyl-1-oxa-cycloheptan-2-one (6) as a clear light yellow oil (24.2 g, 91%): ir (neat) 1720 cm⁻¹ (lactone); nmr (CDCl₃) δ1.42 (s, 3H, CH₃), 2.64 (m, 2H, OC—CH- $_2$—CH$_2$), 3.50 (m, 2H, O—C$\underline{H}$$_2$—CH$_2$), 4.50 (s, 2H, O—C$\underline{H}$$_2$—Ph), 7.32 (s, 5H, aromatic).

EXAMPLE 6

Diethyl [2-(4'-benzyloxybutyl)-2-methyl-3(H), 4,5-dihydrooxepinyl]-7-phosphate (7)

A solution of 7-(4'-benzyloxybutyl)-7-methyl-1-oxacycloheptan-2-one (24.2 g, 0.0834 mol) in dry tetrahydrofuran (100 ml) is added dropwise to a lithium diisopropylamide solution [prepared from n-butyllithium in hexane (78 ml, 0.125 mol) and diisopropylamine (12.6 g, 0.125 mol)] in dry tetrahydrofuran (600 ml) with hexamethylphosphoric triamide (22.4 g, 0.125 mol) cooled to $-78°$ C. After stirring for 45 minutes, tetramethylethylenediamine (200 ml) is added followed by diethyl chlorophosphate (21.6 g, 0.125 mol) in tetrahydrofuran (100 ml). The cooling bath is removed and stirring at room temperature is maintained for 0.5 hours. The reaction mixture is poured into pH-7 phosphate buffer (750 ml) and extracted with ether (5×100 ml). The ether phases are combined, dried (MgSO$_4$) and the solvent is removed under reduced pressure. The crude product is chromatographed on SilicAR CC-7 (700 g) in hexane. Elution with 20% ethyl acetate/hexane gives diethyl [2-(4'-benzyloxybutyl)-2-methyl-3(H), 4,5-dihydrooxepinyl]-7-phosphate (7) as a clear light yellow oil (30.2 g, 95%).

EXAMPLE 7

2-(4'-Hydroxybutyl)-2-methyl-6-oxepene (8)

t-Butyl alcohol (94.6 g, 1.28 mol) is added to a freshly distilled solution of ammonia (2000 ml) cooled to $-78°$ in an argon atmosphere. The cooling bath is removed and diethyl [2-(4'-benzyloxybutyl)-2-methyl-3(H), 4,5-dihydrooxepinyl]-7-phosphate (30.2 g, 0.07 mol) in tetrahydrofuran (500 ml) is added. Freshly cut sodium metal (8.25 g, 0.359 mol) is added in small pieces at $-33°$ C. The resulting blue solution is stirred for 0.5 hours and quenched by the addition of ether (1000 ml) followed by water (100 ml). The ammonia is evaporated at room temperature and the ether layer is separated. The water phase is extracted with ether (5×100 ml), the ether phases are combined, washed with satd. NaCl (500 ml), dried (MgSO$_4$) and the solvent is removed under reduced pressure. The crude product (13.2 g) is chromatographed on SilicAR CC-7 (250 g) in hexane. Elution with 10% ethyl acetate/hexane gives 2-(4'-hydroxybutyl)-2-methyl-6-oxepene (8) as a clear light yellow oil (6.6 g, 51%); ir (neat) 3400 cm$^{-1}$ (OH); nmr (CDCl$_3$) $\delta$1.22 (s, 3H, CH$_3$), 3.62 (m, 2H, HO—C$\underline{H}$$_2$—CH$_2$), 4.48 (m, 1H, J-6 Hz, O—CH=C$\underline{H}$—CH$_2$), 6.00 (d, 1H, J=6 Hz, —O—C$\underline{H}$=CH).

EXAMPLE 8

2-(4'-Benzyloxybutyl)-2-methyl-6-oxepene (9)

2-(4'-Hydroxybutyl)-2-methyl-6-oxepene (6.6 g, 0.0358 mol) in benzene (50 ml) is added to a suspension of sodium hydride (3.44 g, 0.0716 mol, 50% dispersion in oil, previously washed with hexane) in benzene (200 ml), in a nitrogen atmosphere. After 0.5 hour, benzyl bromide (8.55 g, 0.05 mol) in benzene (25 ml) is added. The mixture is refluxed for 16 hours, cooled and poured into satd. NaCl (250 ml). The aqueous layer is extracted with ether (3×25 ml). The organic phases are combined, dried (MgSO$_4$) and the solvents are removed under reduced pressure. The crude product (10.4 g) is chromatographed on SilicAR CC-7 (150 g) in hexane. Elution with 4% ethyl acetate/hexane gives 2-(4'-benzyloxybutyl)-2-methyl-6-oxepene as a clear colorless oil (9.8 g, 99%).

EXAMPLE 9

2-(4'-Benzyloxybutyl)-2-methyl-oxepane-6-ol (10)

Boron hydride (11.9 ml, 1 M solution in tetrahydrofuran, 0.0119 mol) is added to a solution of 2-(4'-benzyloxybutyl)-2-methyl-6-oxepane (9.80 g, 0.0358 mol) in tetrahydrofuran (250 ml) at 0° C. in a nitrogen atmosphere. The cooling bath is removed and the mixture is stirred for 2 hours at 25° C. The reaction mixture is quenched by adding 3N NaOH (6.6 ml, 0.02 mol) followed by hydrogen peroxide 30% (4.9 g, 0.043 mol). The resulting mixture is then stirred at 25° C. for 1.5 hours and then poured into satd. NaCl (500 ml). The aqueous phase is extracted with ether (3×100 ml), the ether phases are combined, dried (MgSO$_4$) and the solvents are removed at reduced pressure. The crude product (11.6 g) is chromatographed on SilicAR CC-7 (250 g) in hexane. Elution with 25% ethyl acetate/hexane gives 2-(4'-benzyloxybutyl)-2-methyloxepane-6-ol (10) as a clear colorless oil (6.9 g, 66%): ir (neat) 3350 cm$^{-1}$ (OH); nmr (CDCl$_3$) $\delta$1.18 (s, 3H, CH$_3$), 2.50 (m, 1H, —CH$_2$—C$\underline{H}$—OH—CH$_2$), 3.58 (m, 5H, O—CH$_2$—CH—OH, OH and O—C$\underline{H}$$_2$—CH$_2$), 4.50 (s, 2H, O—C$\underline{H}$$_2$—Ph), 7.32 (s, 5H, aromatic).

EXAMPLE 10

2-(4'-Benzyloxybutyl)-2-methyl-oxepan-6-one (11)

Dry celite (50 g) and 2-(4'-benzyloxybutyl)-2-methyloxepane-6-ol (6.9 g, 0.02 mol) in methylene chloride are added to a pyridine-chromium trioxide solution [prepared from pyridine (22.4 g, 0.284 mol) and chouromium trioxide (14.2 g, 0.142 mol)] in dry methylene chloride (800 ml) at 10° C. in a nitrogen atmosphere. After 2 hours of stirring the mixture is filtered and the celite cake is washed with methylene chloride (10×50 ml). The solvent is removed at reduced pressure. The residue is diluted with ether (200 ml), filtered and the solvent is removed at reduced pressure. The crude product is chromatographed on SilicAR CC-7 (150 g) in hexane. Elution with 10% ethyl acetate/hexane gives 2-(4'-benzyloxybutyl)-2-methyl-oxepan-6-one (11) as a clear colorless oil (5.9 g, 86%).

EXAMPLE 11

2-(4'-Benzyloxybutyl)-6,6-ethylenedioxy-2-methyloxpane (12)

p-Toluenesulfonic acid (200 mg) is added to a solution of 2-(4'-benzyloxybutyl)-2-methyl-oxepan-6-one (5.9 g, 0.021 mol), ethylene glycol (30 ml) and dry benzene (200 ml) and the mixture is refluxed for 17 hours in a nitrogen atmosphere with a Dean-Stark apparatus. The solution is cooled and poured into a satd. NaHCO$_3$ solution. The benzene layer is separated and the aqueous phase is extracted with ether (3×50 ml). The organic layers are combined, dried (MgSO$_4$) and the solvents removed at reduced pressure. The crude product is chromatographed on SilicAR CC-7 (125 g) in hexane. Elution with 10% ethyl acetate/hexane gives 2-(4'-benzyloxybutyl)-6,6-ethylenedioxy-2-methyloxepane as a clear colorless oil (6.7 g, 99%): nmr (CDCl$_3$) $\delta$1.10 (s., 3H, CH$_3$), 3.5 (m, 4H, O—CH$_2$ —and O—CH$_2$—CH$_2$), 3.96 (s, 4H, ketal) 4.48 (s, 2H, O—C$\underline{H}$$_2$—Ph), 730 (s, 5H, aromatic).

EXAMPLE 12

6,6-Ethylenedioxy-2-(4'-hydroxybutyl)-2-methyloxepane (13)

t-Butyl alcohol (8.88 g, 0.12 mol) is added to freshly distilled ammonia (360 ml) cooled to 78° C. in an argon atmosphere. The cooling bath is removed and 2-(4'-benzyloxybutyl)-6,6-ethylenedioxy-2-methyloxepane (6.7 g, 0.02 mol) in tetrahydrofuran (90 ml) is added. Freshly cut sodium metal (1.0 g, 0.04 mol) is added in small pieces and the resulting blue solution is stirred for 30 minutes. The reaction is quenched by adding ether (350 ml) followed by water (5 ml). The ammonia is evaporated at room temperature and the ether phase is washed with satd. NaCl (300 ml). The aqueous phase is extracted with ether (5×100 ml). The ether phases are combined, dried (MgSO$_4$) and the solvents are removed under reduced pressure to give 6,6-ethylenedioxy-2-(4'-hydroxybutyl)-2-methyloxepane (13) (4.88 g, 99%): nmr (CDCl$_3$) δ1.18 (s, 3H, CH$_3$), 1.30 (s, 1H, OH), 3.42 (s, 2H, —O—$\underline{CH}_2$), 3.60 (m, 2H, HO—$\underline{CH}_2$—CH$_2$) 3.98 (s, 4H, ketal).

EXAMPLE 13

6,6-Ethylenedioxy-2-methyl-2-(4'-oxobutyl)-oxepane (14)

Dry celite (40 g) and 6,6-ethylenedioxy-2-(4'-hydroxybutyl)-2-methyloxepane (4.88 g, 0.0196 mol) in methylene chloride (100 ml) are added to a pyridine-chromium trioxide solution [prepared from pyridine (18.6 g, 0.0284 mol) and chromium trioxide (11.8 g, 0.118 mol)] in dry methylene chloride (500 ml) at 10° C. in a nitrogen atmosphere. After 5 hours the mixture is filtered and the celite is washed with methylene chloride (10×50 ml). The solvent is removed at reduced pressure. The residue is diluted with ether (200 ml), filtered and the ether is removed at reduced pressure. The crude product (4.7 g) is chromatographed on SilicAR CC-7 (100 g) in hexane. Elution with 20% ethyl acetate/hexane gives 6,6-ethylenedioxy-2-methyl-2-(4'-oxobutyl)-oxepane (14) as a clear colorless oil (3,3 g, 70%): ir (neat) 1725 cm$^{-1}$ (CHO).

EXAMPLE 14

6,6-Ethylenedioxy-2-(4'-hydroxypentyl)-2-methyloxepane (15)

Methyllithium (10 ml, 0.0184 mol, 1.84 M in hexane) is added dropwise to a solution of 6,6-ethylenedioxy-2-methyl-2-(4'-oxobutyl)-oxepane (3.3 g) in ether (150 ml) at 0° C. in a nitrogen atmosphere. The cooling bath is removed and the mixture is stirred for 0.5 hour at ambient temperature. The mixture is poured into cold satd. NaCl (300 ml). The ether layer is separated and the aqueous layer extracted with ether (3×50 ml). The ether phases are combined, dried (MgSO$_4$) and the solvent is removed at reduced pressure. The crude product (3.6 g) is chromatographed on SilicAR CC-7 (70 g) in hexane. Elution with 15% ethyl acetate/hexane gives 6,6-ethylenedioxy-2-(4'-hydroxypentyl)-2-methyloxepane (15) as a clear colorless oil (3.3 g, 94%).

EXAMPLE 15

6,6-Ethylenedioxy-2-methyl-2-(4'-oxopentyl)-oxepane (16)

Dry celite (30 g) and 6,6-ethylenedioxy-2-(4'-hydroxypentyl)-2-methyloxepane (3.3 g, 0.0128 mol) in methylene chloride (50 ml) are added to a pyridine-chromium trioxide solution [prepared from pyridine (12.1 g, 0.153 mol) and chromium trioxide (7.67 g, 0.0767 mol)] in distilled methylene chloride (450 ml) at 10° C. in a nitrogen atmosphere. After 5 hours the mixture is filtered and the celite cake is washed with methylene chloride (10×50 ml). The solvent is removed at reduced pressure. The residue is diluted with ether (150 ml), filtered and the solvent is removed at reduced pressure. The crude product (3.3 g) is chromatographed on SilicAR CC-7 (60 g) in hexane. Elution with 12% ethyl acetate/hexane gives 6,6-ethylenedioxy-2-methyl-2-(4'-oxopentyl)-oxepane as a clear colorless oil (2.1 g, 64%).

EXAMPLE 16

6,6-Ethylenedioxy-2-methyl-2-(4'-methyl-4'-pentenyl)-oxepane (17)

A suspension of sodium hydride (2.0 g, 0.041, 50% dispersion in oil previously washed with pentane) in dimethylsulfoxide (40 ml) is heated to 70° C. under a nitrogen atmosphere and stirred for 45 minutes. The mixture is cooled to 25° C. and (Ph)$_3$P$^+$CH$_3$I$^-$ (16.5 g, 0.041 mol) in dimethylsulfoxide (30 ml) is added. The mixture is stirred for 30 minutes and 6,6-ethylenedioxy-2-methyl-2-(4'-oxopentyl)-oxepane (16) (2.1 g, 0.0082 mol) in dimethylsulfoxide (20 ml) is added. The mixture is heated to 60° C. After 4 hours, the reaction mixture is cooled, added to satd NaCl (500 ml) and the mixture is extracted with ether (6×100 ml). The ether layers are combined, dried (MgSO$_4$) and the solvent is removed under reduced pressure. The crude product (5.3 g) is chromatographed on SilicAR CC-7 (40 g) in hexane. Elution with 5% ethyl acetate/hexane gives 6,6-ethylenedioxy-2-methyl-2-(4'-methyl-4'-pentenyl)-oxepane as a light yellow oil (2.1 g, 99%): nmr (CDCl$_3$) δ1.10 (s, 3H, CH$_3$), 3.4 (s, 2H, O—$\underline{CH}_2$—C), 3.98 (s, 4H, ketal) 4.62 (broad s, 2H, $\underline{CH}_2$=C—CH$_3$).

EXAMPLE 17

6,6-Ethylenedioxy-2-methyl-2-(4'-methyl-5'-hydroxypentyl)-oxepane (18)

A solution of 6,6-ethylenedioxy-2-methyl-2-(4'-methyl-4'-pentenyl)-oxepane (2.1 g, 0.0082 mol) in tetrahydrofuran (25 ml) is added to a solution of 9-borabicyclo[3.3.1]-nonane (2.0 g, 0.0164 mol) in tetrahydrofuran (75 ml) at 0° C. The cooling bath is removed and the reaction mixture stirred for 3 hours at 25° C. The reaction is decomposed at 0° C. by adding 3 N NaOH (11 ml) followed by 30% hydrogen peroxide (9.6 g, 0.085 mol). The mixture is stirred for 1.5 hours allowing the temperature to warm to 24° C. The mixture is poured into satd. NaCl (300 ml) and extracted with ether (5×100 ml). The extracts are combined, dried (MgSO$_4$) and the solvent is removed under reduced pressure. The crude product (2.2 g) is chromatographed on SilicAR CC-7 (40 g) in hexane. Elution with 10% ethyl acetate/hexane gives 6,6-ethylenedioxy-2-methyl-2-(4'-methyl-5'-hydroxy pentyl)-oxepane as a clear colorless oil (1.95 g, 87%).

EXAMPLE 18

6,6-Ethylenedioxy-2-methyl-2-(4'-methyl-5'-oxopentyl)-oxepane (19)

A solution of pyridine (6.8 g, 0.086 mol) and chromium trioxide (4.3 g, 0.043 mol) in methylene chloride (450 ml) at 23° C. in a nitrogen atmosphere is stirred for 45 minutes. The mixture is cooled to −20° C. and celite (20 g) is added followed by 6,6-ethylenedioxy-2-methyl-2-(4'-methyl-5'-hydroxypentyl)-oxepane (1.95 g, 0.00717 mol) in methylene chloride (50 ml). The mixture is stirred for 1 hour at −20° C. and 30 minutes at 0° C. The mixture is then filtered and the celite cake is washed with methylene chloride (10×50 ml). The filtrate and washings are combined and washed with satd. NaHCO₃ (2×150 ml). The methylene chloride phase is separated, dried (MgSO₄) and the solvents are removed at reduced pressure. The crude product (1.9 g) is chromatographed on SilicAR CC-7 (50 g) in hexane. Elution with 15% ethyl acetate/hexane gives 6,6-ethylenedioxy-2-methyl-2-(4'-methyl-5'-oxopentyl)-oxepane (19) as a clear colorless oil (1.33 g, 68%): nmr (CDCl₃) δ1.10 (d, J=6 Hz, 3H, C$\underline{H}_3$—CH—CHO), 3.42 (s, 2H, O—C$\underline{H}_2$—C), 3.97 (s, 4H, ketal), 9.53 (d, J=2Hz, 1H, CH—C$\underline{H}$O).

EXAMPLE 19

6,6-Ethylenedioxy-2-methyl-2-(4',8'-dimethyl-5'-hydroxy-8'-nonenyl)-oxepane (20)

A solution of 4-bromo-3-methyl-1-butene (1.15 g, 0.0077 mol) in anhydrous tetrahydrofuran (8 ml) is added dropwise over 2 hours to a suspension of magnesium turnings (192 mg, 0.0079 mol) in anhydrous tetrahydrofuran (10 ml). After stirring for 1 hour, the solution is cooled to −5° to −10° C. and a solution of 6,6-ethylenedioxy-2-methyl-2-(4'-methyl-5'-oxopentyl)-oxepane (1.33 g, 0.00493 mol) in tetrahydrofuran (7 ml) is added dropwise over a period of 30 minutes. The mixture is allowed to warm to 24° C. and is stirred for 30 minutes, quenched with water (5 ml), poured into satd. NaCl and extracted with ether (5×200 ml). The organic layers are combined, dried (MgSO₄) and evaporated in vacuo to give 1.8 g of a viscous, light yellow oil which is chromatographed on SilicAR CC-7 (50 g) in hexane. Elution with 10–15% ethyl acetate/hexane gives 6,6-ethylenedioxy-2-methyl-2-(4',8'-dimethyl-5'-hydroxy-8'-nonenyl)-oxepane (20) as a colorless oil (1.5 g, 90%): nmr (CDCl₃) δ0.90 (d, J=6 Hz, 3H, CH—C$\underline{H}_3$) 1.18 (s, 3H, CH₃), 1.72 (s, 3H,

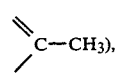

3.42 (s, 2H,

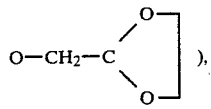

3.98 (s, 4H, ketal), 4.67 (C=C$\underline{H}_2$).

EXAMPLE 20

6,6-Ethylenedioxy-2-methyl-2-(5'-acetoxy-4',8'-dimethyl-8'-nonenyl)-oxepane (21)

A solution of 6,6-ethylenedioxy-2-methyl-2-(4',8'-dimethyl-5'-hydroxy-8'-nonenyl)-oxepane (1.5 g, 0.0044 mol) in pyridine (10 ml) and acetic anhydride (2.7 ml) is stirred under nitrogen at 24° C. for 24 hours. The reaction mixture is poured into water and stirred for 1.5 hr. The residue is taken up into ether (5×100 ml), washed with H₂O, satd NaHCO₃, H₂O and satd. NaCl, dried (MgSO₄), and evaporated in vacuo to give 1.5 g of a thick, yellow oil which is chromatographed on SilicAR CC-7 (35 g) in hexane. Elution with 5–9% ethyl acetate/hexane gives 6,6-ethylenedioxy-2-methyl-2-(5'-acetoxy-4',8'-dimethyl-8'-nonenyl)-oxepane (21) (1.46 g, 87%): nmr (CDCl₃) δ0.95 (d, J=6 Hz, 3H, —CH—C$\underline{H}_3$), 1.18 (s, 3H, CH₃), 2.01 (s, 3H, OAc), 3.42 (s, 2H,

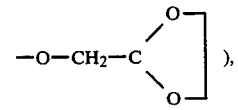

3.97 (s, 4H, ketal), 4.66 (broad s, 2H,—C=C$\underline{H}_2$), 4.80 (m, 1H, C$\underline{H}$—OAc).

EXAMPLE 21

6,6-Ethylenedioxy-2-methyl-2-(5'-acetoxy-4',8'-dimethyl-7'-nonenyl)-oxepane (22)

A solution of 6,6-ethylenedioxy-2-methyl-2-(5'-acetoxy-4',8'-dimethyl-8'-nonenyl)-oxepane (1.46 g, 0.0038 mol) and p-toluenesulfonic acid (100 mg) in anhydrous benzene (100 ml) is refluxed for 18 hours under a nitrogen atmosphere. The mixture is cooled to room temperature, diluted with ether (350 ml), washed with satd. NaHCO₃, H₂O, satd. NaCl, dried (MgSO₄) and evaporated in vacuo to give 6,6-ethylenedioxy-2-methyl-2-(5'-acetoxy-4',8'-dimethyl-7'-nonenyl)-oxepane (1.43 g, 98%) as a viscous, light yellow oil: nmr (CDCl₃) 0.90 (d, J=7 Hz, 3H, HC—CH₃), 1.10 (s, 3H, CH₃), 2.00 (s, 3H, OAc), 3.42 (s, 2H, O—C$\underline{H}_2$—

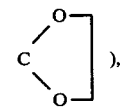

3.98 (s, 4H, ketal), 4.59–5.26 (m, 2H, >C=CH and C$\underline{H}$—OAc).

EXAMPLE 22

2-Methyl-2-(5'-acetoxy-4',8'-dimethyl-7'-nonenyl)-oxepan-6-one (23)

A solution of 6,6-ethylenedioxy-2-methyl-2-(5'-acetoxy-4',8'-dimethyl-7'-nonenyl)-oxepane (1.43 g, 0.0037 mol), p-toluenesulfonic acid (200 mg) and water (7.5 ml) in acetone (45 ml) is refluxed for 5 hours. The mixture is cooled to room temperature, diluted with ether (200 ml), washed with H₂O, satd. NaHCO₃, H₂O, satd. NaCl, dried (MgSO₄) and evaporated in vacuo to give 1.32 g of a viscous yellow oil which is chromatographed on SilicAR CC-7 (30 g) in hexane. Elution with 2–5% ethyl acetate/hexane gives 2-methyl-2-(5'-acetoxy-4',8'-dimethyl-7'-nonenyl-oxepan-6-one as a heavy, colorless oil (950 mg, 90%); nmr (CDCl₃) δ0.88 (d, J=6 Hz, 3H, CH—C$\underline{H}_3$), 1.18 (s, 3H, CH₃), 2.00 (s, 3H, OAc), 262 (m, 2H, CO—C$\underline{H}_2$—CH₂), 3.98 (s, 2H, O—C$\underline{H}_2$—CO), 4.60–5.20 (m, 2H, >C=C$\underline{H}$ and C$\underline{H}$—OAc).

EXAMPLE 23

2-(5'-Acetoxy-4',8'-dimethyl-7'-nonenyl)-2-methyl-6-(2'-carboethoxymethyl)-6-oxepene (24) and 2-(5'-Acetoxy-4',8'-dimethyl-7'-nonenyl)-2-methyl-6-(2'-carboethoxymethylidene)-oxepane (25)

Triethylphosphonoacetate (2.5 g, 0.0111 mol) in benzene (10 ml) is added to a suspension of sodium hydride (0.53 g, 0.0111 mol, of a 50% mineral oil dispersion freshly washed with hexane and benzene) in benzene (50 ml) in a nitrogen atmosphere. The mixture is heated to 70° C. and stirred for 15 minutes. The mixture is then cooled to 25° C. and 2-methyl-2-(5'-acetoxy-4',8'-dimethyl-7'-nonenyl)-oxepan-6-one (1.25 g, 0.037 mol) in benzene (20 ml) is added. The mixture is heated to 70° C., stirred for 1 hour and then cooled to 25° C., diluted with ether (25 ml) and quenched with water (5 ml). The resulting mixture is poured into pH-7 phosphate buffer solution (150 ml) and extracted with ether (5×50 ml). The organic layers are combined, dried (MgSO₄) and evaporated to give a yellow oil (2.30 g) which is chromatographed on SilicAR CC-7 (30 g) in hexane. Elution with 25% ethyl acetate/hexane gives 1.237 g (82%) of a colorless oil which by nmr is shown to be a mixture of 2-(5'-acetoxy-4',8'-dimethyl-7'-nonenyl)-2-methyl-6-(2'-carboethoxymethyl)-6-oxepene and 2-(5'-acetoxy-4',8'-dimethyl-7'-nonenyl)-2-methyl-6-(2'-carboethoxymethylidene)-oxepane: nmr (CDCl₃) δ 5.1 (m, —O—CH₂—C=CH—COOEt), 5.95 (s, —O—CH=C—CH₂—COOEt); mass spectrum for (24), 408 (M+), 362 (M-C₂H₅OH), 348 (M-HOAc), 302 (348-C₂H₅OH), 197 (M-side chain), and for (25) 348, 302 (348-C₂H₅OH), 197 (M-side chain); ratio of 24:25 (~7:3) by GC/MS.

EXAMPLE 24

6-(2'-Hydroxyethyl)-2-methyl-2-(4',8'-dimethyl-5'-hydroxy-7'-nonenyl)-6-oxepene (26) and 6-E and 6-Z 6-(2'-Hydroxyethylidene)-2-methyl-2-(4',8'-dimethyl-5'-hydroxy-7'-nonenyl)-oxepane (27)

A solution of the mixture of 2-(5'-acetoxy-4',8'-dimethyl-7'-nonenyl)-2-methyl-6-(2'-carboethoxymethyl)-6-oxepene and 2-(5'-acetoxy-4',8'-dimethyl-7'-nonenyl)-2-methyl-6-(2'-carboethoxymethylidene)-oxepane (1.04 g, 0.0025 mol) in ether (30 ml) is added dropwise to a suspension of lithium aluminum hydride (104 mg, 0.0025 mol) in ether (10 ml) under nitrogen. After the addition is complete, the mixture is refluxed for 1 hour, cooled to 25° C. and quenched by the addition of wet ether (7 ml). The mixture is diluted with a satd. ammonium chloride solution and extracted with ether (5×20 ml). The ether phases are combined, dried (MgSO₄) and evaporated in vacuo to give 1.1 g of a yellow oil which is chromatographed on SilicAR CC-7 (15 g) in hexane. Elution with 10% ethyl acetate/hexane gives 6-(2'-hydroxyethyl)-2-methyl-2-(4',8'-dimethyl-5'-hydroxy-7'-nonenyl)-6-oxepene as a light yellow oil (540 mg): ir (neat) 3550 cm⁻¹ (OH); nmr (CDCl₃) δ 0.96 (d, 3H, J=6 Hz,

—CH—CH₃), 1.30 (s, 3H, CH₃), 2.19 (t, 4H,

HC=C—CH₂—CH₂, HO—CH—CH₂—CH=), 3.56 (m, 3H, —CH₂—CH₂—OH,

—CH—OH), 5.18 (m, 1H,

\C=CH—CH₂),
/

6.00 (s, 1H,

O—CH=C—),

Mass spectrum, 324 (M+), 306 (M—H₂O), 293 (M—CH₂OH), 237 (306-C₅H₉), 224 (293-C₅H₉). Further elution with 15% ethyl acetate/hexane affords 6E and 6Z 6-(2'-hydroxyethylidene)-2-methyl-2-(4',8'-dimethyl-5'-hydroxy-7'-nonenyl)-oxepane as a clear colorless oil (160 mg): ir (neat) 3550 cm⁻¹ (OH); nmr (CDCl₃) δ 0.91 (d, 3H, J=6 Hz, —CH—CH₃), 1.23 (s, 3H, CH₃), 2.08 (t, 4H, \C=CH—CH₂ and \C=CH—CH₂—CHOH),
/                    /

3.50 (m, 3H,

\C=CH—CH₂—OH and —CH₂—CH—OH—CH—CH₃),
/

4.00 (s, 2H, —O—CH₂—C=), 4.96 to 5.6 (m, 2H,

\C=CH—CH₂OH, \C=CH—CH₂),
/              /

Mass spectrum 324 (M+), 306 (M-H₂O), 288 (306-H₂O), 255 (324-C₅H₉).

I claim:
1. A compound selected from

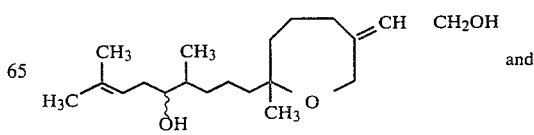

and

-continued

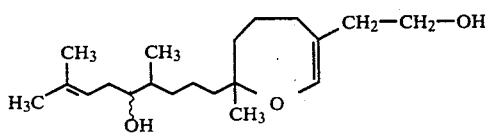

2. A process for the preparation of compounds of claim 1 of the formula

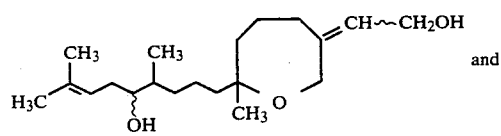 and

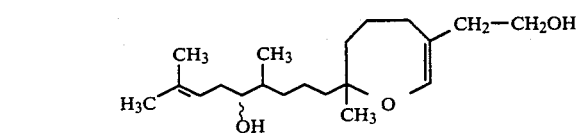

which comprises reacting a compound of the formula

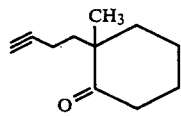

with ethylene glycol to form a ketal of the formula

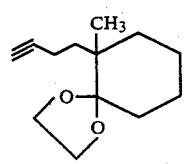

reacting the ketal formed first with 9-borabicyclo-[3.3.1]nonane followed by reaction with a peroxide in aqueous base to form an alcohol of the formula

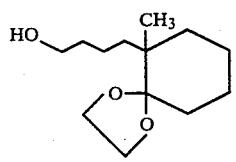

reacting the alcohol first with sodium hydride followed by reaction with benzyl bromide to form a ketal of the formula

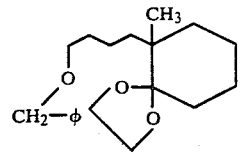

hydrolyzing the ketal with a strong acid to form a ketone of the formula

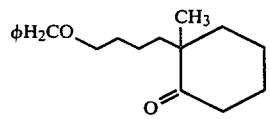

reacting the ketone with a peroxy acid to form a compound of the formula

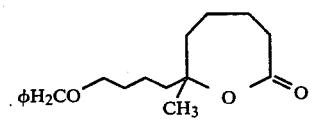

reacting the reaction product first with lithium diisopropylamide then with diethyl chlorophosphate to form a compound of the formula

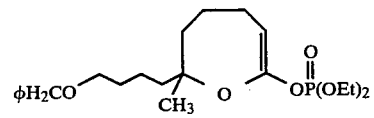

reacting the reaction product formed with sodium in liquid ammonia to form an alcohol of the formula

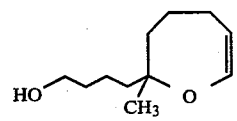

reacting the alcohol with benzyl bromide in the presence of a base to form a compound of the formula

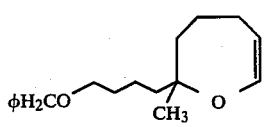

reacting the product formed with diborane to form an alcohol of the formula

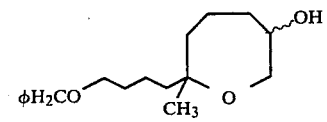

reacting the alcohol with an oxidizing agent to form a ketone of the formula

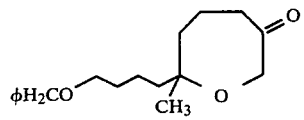

reacting the ketone with ethylene glycol to form a ketal of the formula

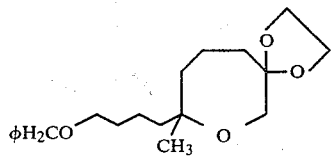

reacting the ketal with sodium in liquid ammonia to form an alcohol of the formula

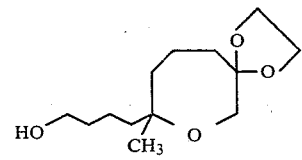

reacting the alcohol with an oxidizing agent to form an aldehyde of the formula

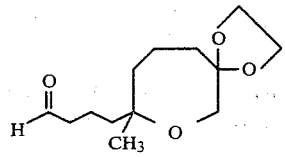

reacting the aldehyde with methyllithium to form an alcohol of the formula

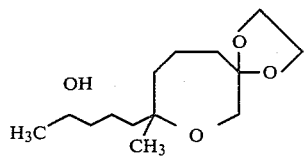

reacting the alcohol with an oxidizing agent to form a ketone of the formula

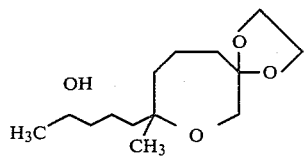

reacting the ketone with triphenylmethylphosphonium iodide in the presence of a base to form a compound of the formula

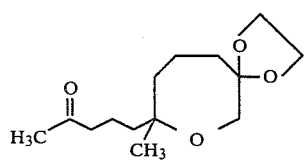

reacting the product formed with 9-borabicyclo[3.3.1-]nonane to form an alcohol of the formula

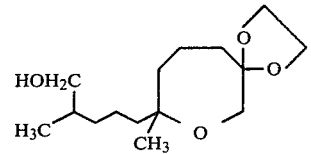

reacting the alcohol with an oxidizing agent to form an aldehyde of the formula

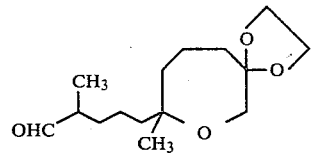

reacting the aldehyde with a Grignard reagent prepared from 4-bromo-3-methyl-1-butene to form a compound of the formula

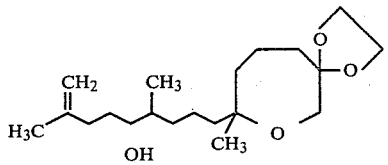

reacting the product formed with an esterifying agent to form a compound of the formula

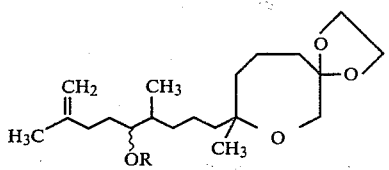

treating the ester formed with p-toluenesulfonic acid to form a compound of the formula

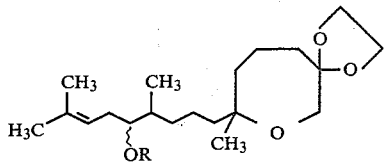

treating the product formed with acid to form a ketone of the formula

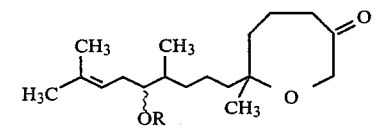

reacting the ketone with triethylphosphonoacetate in the presence of a base to form a mixture of compounds having the following formulas

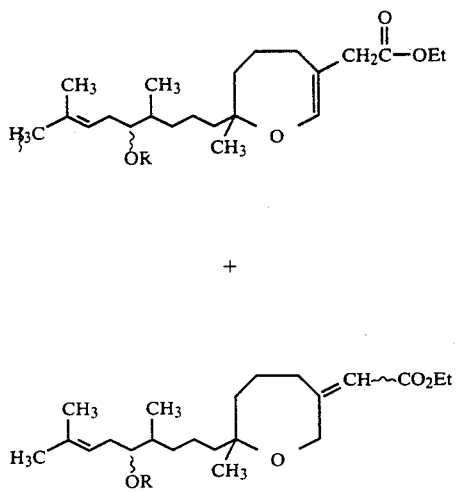

+ reacting the mixture of compounds with lithium aluminum hydride to obtain a mixture of alcohols having the following formulas

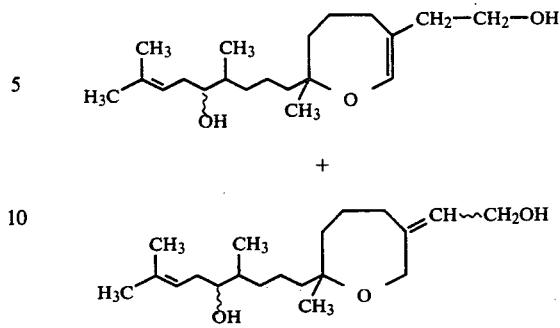

+ and separating the mixture, wherein R is a lower alkanoyl group having 2–5 carbon atoms.

3. The process of claim 2 wherein the esterifying agent is acetic anhydride.

4. The process of claim 2 wherein the peroxide is hydrogen peroxide.

5. The process of claim 2 wherein the peroxy acid is m-chloroperoxybenzoic acid.

6. The process of claim 2 wherein the base is sodium hydride.

7. The process of claim 3 wherein the oxidizing agent is chromium trioxide/pyridine.

8. The process of claim 2 wherein the acid is p-toluenesulfonic acid.

* * * * *

UNITED STATES PATENT AND TRADEMARK OFFICE
CERTIFICATE OF CORRECTION

PATENT NO. : 4,384,126

DATED : May 17, 1983

INVENTOR(S) : Vinayak V. Kane

It is certified that error appears in the above—identified patent and that said Letters Patent is hereby corrected as shown below:

Column 16, line 65

" 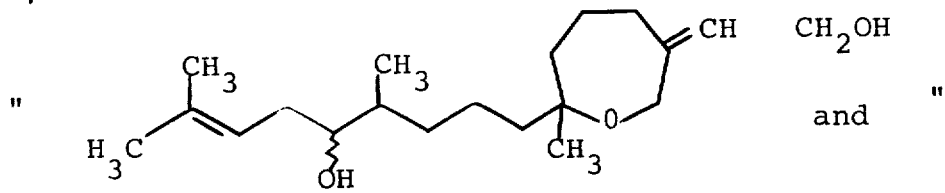 and "

should be 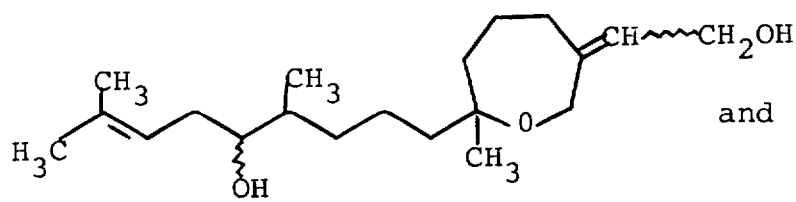 and

Column 19, line 40

" 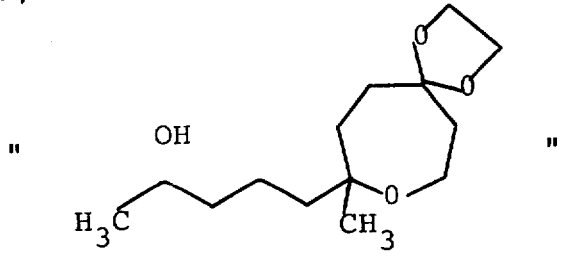 "

should be 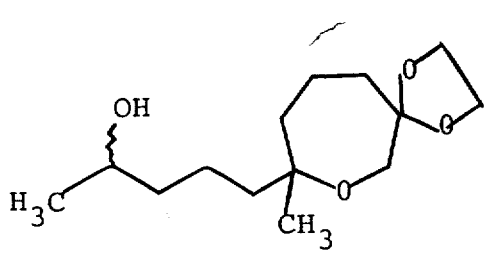

UNITED STATES PATENT AND TRADEMARK OFFICE
CERTIFICATE OF CORRECTION

PATENT NO. : 4,384,126

DATED : May 17, 1983

INVENTOR(S) : Vanayak V. Kane

It is certified that error appears in the above—identified patent and that said Letters Patent is hereby corrected as shown below:

Column 20, line 30

" 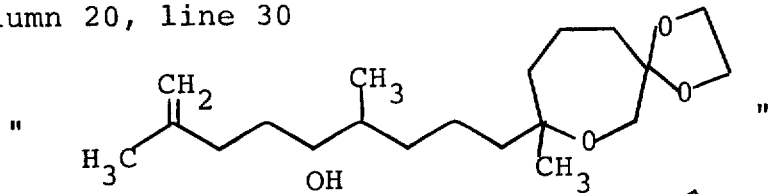 "

should be

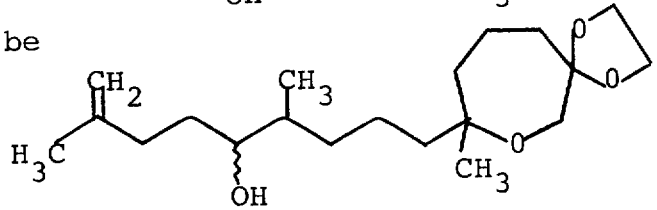

Column 22, line 26, "claim 3" should read -- claim 2 --.

Signed and Sealed this

Thirtieth Day of August 1983

[SEAL]

Attest:

Attesting Officer

GERALD J. MOSSINGHOFF

Commissioner of Patents and Trademarks